United States Patent [19]

Yasuzawa et al.

[11] Patent Number: 5,004,833
[45] Date of Patent: Apr. 2, 1991

[54] KS-501 DERIVATIVES

[75] Inventors: Toru Yasuzawa, Sakai; Satoshi Nakanishi, Machida; Chikara Murakata, Asaka, all of Japan; Hiroshi Kase, Eastham, England; Hiroshi Sano; Koji Yamada, both of Machida, Japan

[73] Assignee: Kyowa Hakko Kogyo Co., Ltd., Tokyo, Japan

[21] Appl. No.: 408,192

[22] Filed: Sep. 15, 1989

[30] Foreign Application Priority Data

Sep. 21, 1988 [JP]  Japan ................................ 63-237316
Sep. 21, 1988 [JP]  Japan ................................ 63-237317

[51] Int. Cl.$^5$ .................... C07H 15/00; A61K 31/715
[52] U.S. Cl. ..................................... 536/18.2; 536/4.1; 536/115; 514/25; 514/532; 514/533; 514/544
[58] Field of Search ................. 514/25, 532, 533, 544; 536/4.1, 18.2, 115

[56] References Cited

U.S. PATENT DOCUMENTS 4,801,697  1/1989  Yaginuma et al. ................. 536/4.1

FOREIGN PATENT DOCUMENTS 0282322  9/1988  European Pat. Off. .
2579599 10/1986  France .
61-195689 8/1986  Japan .

OTHER PUBLICATIONS

Prostaglandins, vol. 24, No. 1, pp. 21–34 (Jul. 1981).
Chemical Abstracts, vol. 102, No. 9, Abstract No. 75671c (1985).
Chemical Abstracts, vol. 107, No. 1, Abstract No. 4264q (1987).
Chemical Abstracts, vol. 111, No. 3, Abstract No. 20565b (1989).
Chem. Pharm. Bull., vol. 28, 3157–3162 (1980).
J. Antibiot, vol. 37, 469–474 (1984).
J. Antibiot, vol 37, 1153–1160 (1984).
Agric. Biol. Chem., vol. 50, 2723–2727 (1986).

*Primary Examiner*—Ronald W. Griffin
*Assistant Examiner*—Nancy S. Carson
*Attorney, Agent, or Firm*—Fitzpatrick, Cella, Harper & Scinto

[57] ABSTRACT

Disclosed are KS-501 derivatives represented by the formula (I)

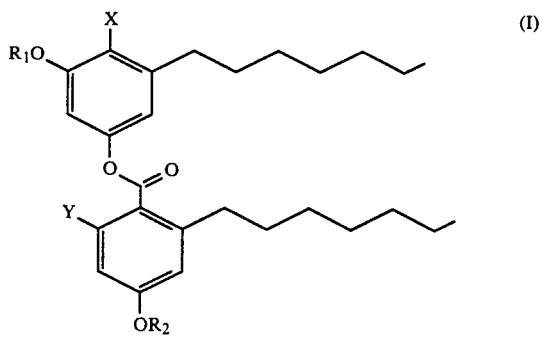

wherein X represents a hydrogen atom or $COOR_3$, Y represents hydroxy or

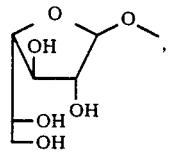

and $R_1$, $R_2$ and $R_3$ are the same or different and represent a hydrogen atom or an alkyl group having 1 to 4 carbon atoms, provided that when $R_1$, $R_2$ and $R_3$ are simultaneously hydrogen atoms, and when $R_1$, $R_2$ and X are simultaneously hydrogen atoms, Y does not represent

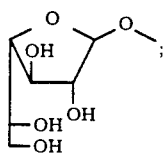

and a pharmaceutically acceptable acid addition salt thereof. The KS-501 derivatives have a platelet aggregation-inhibiting property, and are expected to be useful as antithrombotic agent.

4 Claims, No Drawings

KS-501 DERIVATIVES

BACKGROUND OF THE INVENTION

The present invention relates to KS-501 derivatives and pharmaceutically acceptable acid addition salts thereof.

The KS-501 derivatives and pharmaceutically acceptable acid addition salts thereof have a platelet aggregation-inhibiting property and are thus useful as antithrombotic agent, etc.

As substances having a platelet aggregation-inhibiting property, aspirin, indomethacin, dazoxiben, prostaglandin $I_2$, prostaglandin $E_1$, ticlopidine, papaverine and dipyridamole are known.

Further, the following compounds are reported.

Pyrrothines
 Chem. Pharm. Bull. 28, 3157–3162 (1980)

thiolutin: R = CH$_3$
aureothricin: R = CH$_2$CH$_3$
isobutyropyrrothine: R = CH(CH$_3$)$_2$ WF-5239
 J. Antibiot. 37, 469–474 (1984)

WF-30581
 J. Antibiot. 37, 1153–1160 (1984)

WF-30581A: R = CH$_2$CH$_2$CH$_3$
WF-30581B: R = CH$_2$CH$_2$CH$_2$CH$_3$

KS-290IIi-2
 Japanese Published Unexamined Patent Application No. 195689/86

Staurosporine
 Agric. Biol. Chem. 50, 2723–2727 (1986)

KS-501 and KS-502
EP-A-282322

Me: CH$_3$

KS-501: R = H
KS-502: R = COOH

SUMMARY OF THE INVENTION

The primary object of the present invention is to provide compounds having a platelet aggregation-inhibiting property and pharmaceutically acceptable acid addition salts thereof.

In accordance with the present invention, there is provided KS-501 derivatives represented by the formula (I)

wherein X represents a hydrogen atom or COOR$_3$, Y represents hydroxy or

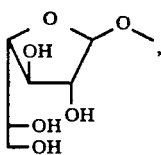

and $R_1$, $R_2$ and $R_3$ are the same or different and represent a hydrogen atom or an alkyl group having 1 to 4 carbon atoms, provided that when $R_1$, $R_2$ and $R_3$ are simultaneously hydrogen atoms, and when $R_1$, $R_2$ and X are simultaneously hydrogen atoms, Y does not represent

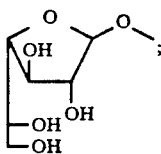

and a pharmaceutically acceptable acid addition salt thereof.

DETAILED DESCRIPTION OF THE INVENTION

The alkyl group having 1 to 4 carbon atoms includes methyl, ethyl, propyl, etc.

The pharmaceutically acceptable acid addition salts thereof include sodium salt, potassium salt, ammonium salt, salts with amines, etc.

Specific examples of KS-501 derivatives of the present invention are shown in Table 1.

Compounds 1 to 4 correspond to compounds obtained in Examples 1 to 4.

TABLE 1

| Compound | Formula |
|---|---|
| 1 | (structure shown) |
| 2 | (structure shown) |
| 3 | (structure shown) |
| 4 | (structure shown) |

Methods for preparing KS-501 derivatives represented by the formula (I) are shown below.

Step 1

A KS-501 derivative represented by the formula (I) wherein X is $COOR_3$, $R_3$ is alkyl having 1 to 4 carbon atoms, and $R_1$ and $R_2$ are hydrogen atoms, can be obtained either by reacting KS-502 with trimethylsilyldiazomethane in a suitable solvent at 0° to 50° C. for 1 to 15 hours, or by subjecting KS-502 to reaction in a lower alcohol in the presence of an acid catalyst at −20° to 40° C. for 5 minutes to 2 hours.

The suitable solvent includes methanol, ethanol, ether, tetrahydrofuran, dioxane, acetone, ethyl acetate, benzene, toluene, chloroform, water, etc., and these solvents can be used alone or in combination. Lower alcohols include methanol, ethanol, propanol, isopropanol, butanol, etc. Acid catalysts include hydrogen chloride, sulfuric acid, phosphoric acid, para-toluenesulfonic acid, methanesulfonic acid, etc.

Step 2

A KS-501 derivative represented by the formula (I) wherein X is a hydrogen atom and $R_1$ and $R_2$ are alkyl having 1 to 4 carbon atoms, or a KS-501 derivative represented by the formula (I) wherein X is $COOR_3$ and $R_1$, $R_2$ and $R_3$ are alkyl having 1 to 4 carbon atoms can be obtained by reacting KS-501, KS-502 or a compound represented by the formula (I) wherein X is $COOR_3$, $R_3$ is alkyl having 1 to 4 carbon atoms and $R_1$ and $R_2$ are hydrogen atoms, prepared according to step 1, with an alkylating agent in a suitable solvent.

The suitable solvent is used the same solvents as mentioned in step 1. The alkylating agent includes diazomethane, diazoethane, etc. Usually, these alkylating agents are used in the form of an ether solution.

Compounds prepared according to steps 1 and 2 can be purified by silica gel column chromatography, preparative thin layer chromatography, high performance liquid chromatography or recrystallization from an organic solvent.

Compound 4 can be prepared by reacting KS-501 with an acid in water or a suitable organic solvent at 0° to 100° C. for 5 minutes to 2 hours. The suitable organic solvent includes methanol, ethanol, isopropanol, tetrahydrofuran and dioxane, aqueous solution of these solvents, etc. The acid includes hydrochloric acid, sulfuric acid, nitric acid, phosphoric acid, anhydrous hydrogen chloride-methanol solvent, etc. Usually, it is most preferred to carry out the reaction in anhydrous hydrogen chloride-methanol at 10° to 30° C. for 10 minutes to one hour. Isolation and purification of the product are carried out by methods used in usual organic synthesis, for example by a combination of extraction, crystallization, chromatography, etc.

The platelet aggregation-inhibiting effect of compound 4 is demonstrated below by Experimental example.

EXPERIMENTAL EXAMPLE

Effect on platelet aggregation (1) Method 8.5 vol of blood was collected from the carotid arteries of a white rabbit, and placed in a tube containing 1.5 vol of a citrate-dextrose solution (71 mM citric acid, 85 mM sodium citrate and 111 mM dextrose). The thus obtained blood was centrifuged at 200 xg for 15 minutes to obtain platelet-rich plasma (PRP). This PRP was centrifuged at 650×g for 10 minutes to obtain platelet precipitates. After washing with $Ca^{++}$-free Tyrode's solution containing 2 mM ethylenebis(oxyethylenenitrilo)tetraacetic acid (hereinafter referred to as EGTA), the platelet precipitates were centrifuged again at 650×g for 10 minutes for washing. The resulting platelet precipitates were suspended in $Ca^{++}$-free Tyrode's solution containing 0.25% bovine serum albumin to reach a density of $5\times10^8$ cells/ml. After allowing to stand for about 30 minutes, 1 mM $CaCl_2$ or 1 mM EGTA was added to the suspension of the washed platelet. The mixture was allowed to stand for further 30 minutes, and then platelet aggregation was measured.

The platelet aggregation was measured with an aggregometer, ACGRETEC TE-500 (product of Erma Optical Co., Ltd.) to which the Born method was applied.

First, 10 μl portions of a test compound solution were added to 0.2 ml portions of the suspension of the washed platelet, while stirring at 1,000 rpm and at 37° C. After incubation at 37° C. for 3 minutes, 10 μl portions of a stimulating agent thrombin (final concentration : 0.05 U/ml) or platelet-activating factor (final concentration: $10^{-10}$ M) were added thereto, respectively to initiate the reaction. The rate of platelet aggregation inhibition of the test compound were calculated from the maximum aggregation rate obtained by the use of the test compound and the maximum aggregation rate obtained by use of only the solvent used for dissolving the test compound, according to the following equation. The effect of the test compound was determined as the drug concentration which gave the inhibition rate of 50%.

$$\text{Inhibition rate (\%)} = \frac{A-B}{A} \times 100$$

A: maximum aggregation rate in use of the solvent alone

B: maximum aggregation rate in use of the test compound (2) Experiment results

TABLE 2

| Stimulating agent | $IC_{50}$ (μg/ml) |
|---|---|
| Thrombin | 72 |
| Platelet-activating factor | 45 |

As is shown in Table 2, compound 4 inhibited platelet aggregation stimulated with thrombin and platelet-activating factor as a stimulating agent.

Certain specific embodiments of the present invention are illustrated by the following examples.

EXAMPLE 1

A diazomethane-ether solution ( 1 ml) obtained by distillation from bis-(N-methyl-N-nitroso)terephthalamide (9 g)/ether (40 ml), was added to a solution of KS-501 (5 mg) in methanol ( 0.5 ml), followed by stirring at room temperature for one hour. The solvent was evaporated under reduced pressure, and the resulting residue was purified by silica gel column chromatography using chloroform:methanol=20:1 v/v as a developing solvent system to obtain compound 1 ( 4 mg) as colorless powder.

Physicochemical properties of compound 1 are set forth below.

SI-MS m/z: $633(M+H)^+$, $471(C_{29}H_{43}O^+)$, $411(C_{21}H_{31}O_8^+)$, $249(C_{15}H_{21}O_3^+)$ $^1$H NMR(400 MHz, in $CD_3OD$): 6.71(1 H, d, J=2.2 Hz), 6.7–6.6(3 H, m), 6.52(1 H, d, J=2.2 Hz), 5.59(1 H, d, J=1.8 Hz), 4.28(1 H, dd, J=3.8, 1.8 Hz), ca.4.15(2 H), 3.82(3 H, s), 3.80(3 H, s), 3.75(1 H, br.t, J=ca.6 Hz), 3.63 and 3.60(2 H, AB in ABX, J=11.2, 7.0, 5.7 Hz), 2.69(2 H, dd, J=9.6, 6.1 Hz), 2.61(2 H, dd, J=8.9, 8.5 Hz), 1.64(4 H, m), 1.4–1.2(16 H, m), 0.89(3 H, t, J=6.9 Hz), 0.87(3 H, t, J=7.0 Hz)

EXAMPLE 2

The same diazomethane-ether solution as in Example 1 was added to a solution of KS-502 ( 5 mg) in methanol (0.5 ml), followed by stirring at room temperature for one hour. The solvent was evaporated under reduced pressure and, the resulting residue was purified by silica gel column chromatography using chloroform:methanol=20:1 v/v as a developing solvent system to obtain compound 2 (4 mg) as colorless powder.

Physicochemical properties of compound 2 are set forth below.

EI-MS m/z: $529(C_{31}H_{45}O_7^+)$, $411(C_{21}H_{31}O_8^+)$, $326(C_{15}H_{18}O_8^+)$, $280(C_{16}H_{24}O_4^+)$, $249(C_{15}H_{21}O_3^+)$, $196(C_{10}H_{12}O_4^+)$ $^1$H NMR(400 MHz, in $CD_3OD$): 6.81(1 H, d, J=2.0 Hz), 6.72(1 H, d, J=2.2 Hz), 6.71(1 H, d, J=2.0 Hz), 6.53 (1 H, d, J=2.2 Hz), 5.60(1 H, d, J=1.7 Hz), 4.27(1 H, dd, J=3.6, 1.7 Hz), ca.4.1(2 H), 3.86(3 H, s), 3.83 (3 H, s), 3.82(3 H, s), ca.3.75(1 H, m), ca.3.6(2 H, AB in ABX), 2.69(2 H, m), 2.56(2 H, m), 1.7–1.5(4 H, m), 1.4–1.2(16 H), 0.89(3 H, t, J=6.7 Hz), 0.87(3 H, t, J=7.1 Hz)

EXAMPLE 3

In this example, 10% trimethylsilyldiazomethanehexane solution (0.019 ml) was added to a solution of KS-502 (6.5 mg) in a mixed solvent of methanol (0.2 ml) and benzene (0.7 ml), followed by stirring at room temperature for 7 hours. The reaction solution was concentrated under reduced pressure, and the residue was purified by preparative silica gel thin layer chromatography using chloroform:methanol=9:1 v/v as a developing solvent system to obtain 2.5 mg of compound 3.

Physicochemical properties of compound 3 are set forth below.

SI-MS m/z: 685(M+Na)$^{30}$, 501, 397, 235

$^1$H NMR(400 MHz, in CDCl$_3$+CD$_3$OD): 6.74(1 H, d, J=2.3 Hz), 6.58(1 H, d, J=2.3 Hz), 6.55(1 H, d, J=2.0 Hz), 6.43 (1 H, d, J=2.0 Hz), 5.67(1 H, br. s), 4.23(2 H, br. s), 4.11(1 H, br. s), 3.87(1 H, m), ca. 3.7(2H, m), 2.89(2 H, m), 2.70(2 H, m), 1.7–1.5(4 H, m), 1.4–1.2 (16 H, m), 0.89(3 H, t, J=7.2 Hz), 0.85(3 H, t, J=7.0 Hz)

EXAMPLE 4

In this example, 10 mg of KS-501 was dissolved in 1 ml of 5% hydrogen chloride-methanol, followed by stirring for one hour. The reaction solution was distributed between ethyl acetate (30 ml) and water (30 ml) layers and the water layer was further extracted twice with 30 ml of ethyl acetate. The ethyl acetate layers were combined, washed with saturated aqueous sodium chloride and dried over magnesium sulfate. After distilling away the solvent under reduced pressure, the resulting residue was subjected to elution on 5 ml of silica gel C-200 (product of Wako Junyaku Kogyo Co., Ltd.) using n-hexane : ethyl acetate (3:1, v/v) to obtain 7 mg of compound 4 as colorless powder (yield: 96%).

Physicochemical properties of compound 4 are set forth below.

EI-MS m/z: 442(M+), 235, 208, 166, 137, 124

$^1$H-NMR (400 MHz, CD$_3$OD, δ): 6.56(1 H, br. t), 6.47(1 H, br. t), 6.44(1 H, t, J=2.5 Hz), 6.28(1 H, d, J=2.5 Hz), 6.22(1 H, d, J=2.5 Hz), 2.90(2 H, m), 2.56(2 H, br. dd), 1.6(4 H, m), 1.4–1.2(16 H, m), 0.89(3 H, t, J=7.0 Hz), 0.84(3 H, t, J=6.9 Hz)

$^{13}$C-NMR(100 MHz, CD$_3$OD, δ): 171.2, 166.0, 164.2, 159.4, 152.3, 149.4, 146.7, 114.2, 113.6, 112.2, 107.4, 105.5, 102.0, 37.8, 36.8, 33.5, 33.0, 32.3, 30.9, 30.3, 30.24, 30.21, 23.7, 14.4

Ultraviolet absorption spectrum: λmax methanol solution 218 nm(ε=31,000), 271 nm(ε=16,000), 304 nm(ε=6,700)

Rf value of compound 4 in thin layer chromatography is indicated in Table 3. Detection was carried out by irradiation with ultraviolet rays of 253.7 nm.

TABLE 3

| Solvent | Rf value |
|---|---|
| n-hexane:ethyl acetate = 2:1 (v/v) | 0.53 |

Thin layer: Art. 5628 made by Merck Co.
Development: room temperature, ascending method, development time: 15 to 40 minutes Thin layer: Art. 5628 made by Merck Co.
Development: room temperature, ascending method, development time: 15 to 40 minutes

What is claimed is:
1. A compound represented by the formula

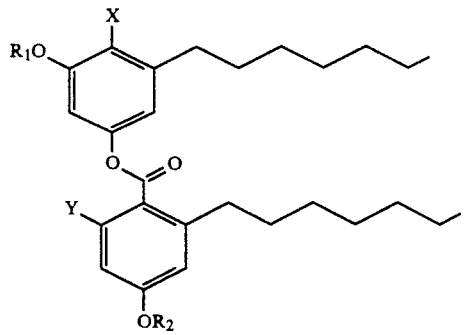

wherein X represents a hydrogen atom or COOR$_3$ wherein R$_3$ represents an alkyl group having 1 to 4 carbon atoms, Y represents hydroxy or

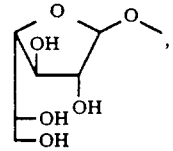

and R$_1$ and R$_2$ are the same or different and represent a hydrogen atom or an alkyl group having 1 to 4 carbon atoms, provided that when R$_1$, R$_2$ and X are simultaneously hydrogen atoms, Y does not represent

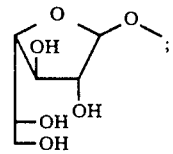

or a pharmaceutically acceptable acid addition salt thereof.

2. The compound according to claim 1, wherein Y is

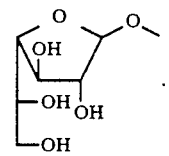

3. The compound according to claim 1, wherein Y is hydroxy.

4. The compound according to claim 1, wherein the pharmaceutically acceptable acid addition salt thereof is selected from the group consisting of sodium salt, potassium salt, ammonium salt and salts with amines.

* * * * *

UNITED STATES PATENT AND TRADEMARK OFFICE
CERTIFICATE OF CORRECTION

PATENT NO. : 5,004,833
DATED : April 2, 1991
INVENTOR(S) : TORU YASUZAWA, ET AL.

It is certified that error appears in the above-identified patent and that said Letters Patent is hereby corrected as shown below:

COLUMN 7

Line 9, "685(M+Na)$^{30}$" should read --685(M+Na)$^{+}$--.
Lines 57-59, delete "Thin layer: Art. 5628 made by Merck Co. Development: room temperature, ascending method, development time: 15 to 40 minutes".

Signed and Sealed this

Twenty-ninth Day of September, 1992

Attest:

DOUGLAS B. COMER

Attesting Officer    Acting Commissioner of Patents and Trademarks